United States Patent
Cooksey

(10) Patent No.: US 9,226,941 B2
(45) Date of Patent: Jan. 5, 2016

(54) TWO-COMPONENT CLEANING AND DISINFECTING SYSTEM

(71) Applicant: Patrick C. Cooksey, Hinsdale, IL (US)

(72) Inventor: Patrick C. Cooksey, Hinsdale, IL (US)

(*) Notice: Subject to any disclaimer, the term of this patent is extended or adjusted under 35 U.S.C. 154(b) by 0 days.

(21) Appl. No.: 14/205,949

(22) Filed: Mar. 12, 2014

(65) Prior Publication Data

US 2015/0320797 A1 Nov. 12, 2015

Related U.S. Application Data

(60) Provisional application No. 61/777,340, filed on Mar. 12, 2013.

(51) Int. Cl.

| | | |
|---|---|---|
| *A61L 9/01* | (2006.01) | |
| *A61L 2/00* | (2006.01) | |
| *C03C 23/00* | (2006.01) | |
| *A61K 33/40* | (2006.01) | |
| *A61K 31/132* | (2006.01) | |
| *A61K 31/14* | (2006.01) | |
| *A61K 31/198* | (2006.01) | |
| *A61K 31/25* | (2006.01) | |
| *A61K 31/08* | (2006.01) | |
| *A61K 31/047* | (2006.01) | |
| *A61K 31/131* | (2006.01) | |
| *A61K 33/00* | (2006.01) | |
| *A61L 2/18* | (2006.01) | |

(52) U.S. Cl.
CPC ............... *A61K 33/40* (2013.01); *A61K 31/047* (2013.01); *A61K 31/08* (2013.01); *A61K 31/131* (2013.01); *A61K 31/132* (2013.01); *A61K 31/14* (2013.01); *A61K 31/198* (2013.01); *A61K 31/25* (2013.01); *A61K 33/00* (2013.01); *A61L 2/186* (2013.01)

(58) Field of Classification Search
CPC ................................ A61L 2/208; A01N 63/00
USPC ............ 422/28, 292; 424/76.8, 616; 510/108; 252/186.41; 134/2
See application file for complete search history.

(56) References Cited

U.S. PATENT DOCUMENTS

2012/0071438 A1* 3/2012 Pedersen ................ A01N 25/16
514/54

* cited by examiner

*Primary Examiner* — Monzer R Chorbaji
(74) *Attorney, Agent, or Firm* — Edward E. Sowers; Brannon Sowers & Cracraft PC

(57) ABSTRACT

A disinfectant, sanitizer, germicide, mildicide, virucide, deodorizer, decontaminator and cleaning formulation for cleaning porous and non-porous materials in hospitals, institutions, farms, hotels, cruise ships, homes, schools and other environments is provided. The cleaning formulation comprises a first component including an aqueous alkaline solution containing a surfactant, a triamine, and a quaternary halide and a second component containing an aqueous stabilized hydrogen peroxide solution. The formulation is activated by combining and mixing the two components. The activated formulation can be applied to a surface to be cleaned and/or sanitized with standard techniques. The two components can also be provided as a disinfectant/sanitizer kit.

18 Claims, No Drawings

TWO-COMPONENT CLEANING AND DISINFECTING SYSTEM

CROSS-REFERENCES TO RELATED APPLICATIONS

This application claims the benefit of U.S. Provisional Patent Application No. 61/777,340, filed Mar. 12, 2013, and entitled TWO-COMPONENT CLEANING AND DISINFECTING SYSTEM, which is incorporated herein by reference.

FIELD OF INVENTION

The present disclosure relates to a two-component formulation capable of cleaning, disinfecting, decontaminating and eliminating odors from a variety of environmental surfaces and methods for the formulation's preparation and use. After their preparation, the two components are mixed just prior to use/application.

BACKGROUND

There is a need for improved means, including formulations and methods, for cleaning and disinfecting surfaces and reducing potential sources of contamination in the home, and in facilities that deal with health services and/or products as well as those that deal with food products and/or services and the like. Such products should exhibit effective cleaning properties, kill a wide range of microorganisms, and generally decontaminate treated surfaces. Our homes and workplaces can also typically become contaminated with a range of harmful and/or unpleasant materials including pesticides, pet and human odors, and other toxic materials derived from building materials and the like. What is needed is a formulation capable of cleaning a surface, effectively eliminating microorganisms, and decomposing or neutralizing a range of harmful and/or unpleasant contaminates in a range of environments including hospitals, institutions, farms, hotels, cruise ships, homes, schools and the like without damaging the treated surface. The present disclosure addresses these needs.

SUMMARY

The present disclosure provides a formulation capable of killing bacteria, viruses, molds, fungi, and the spores of micro-organisms on contact. Additionally, these formulations also decompose, neutralize, or otherwise inactivate reactive compounds that are present in smoke, body odors, animal odors, chemical odors and chemical residues. Finally, a range of toxic materials such as: methamphetamine, phosphorus, iodine, aflatoxin, reactive metals, formaldehyde, pesticides, herbicides, benzopyrenes, nitrosamines, can be destroyed and/or inactivated by the reaction with the formulations disclosed.

One embodiment of the two-component formulation involves a first component (1) which includes an aqueous alkaline solution containing a non-ionic surfactant, at least one quaternary ammonium compound, and a triamine compound; and second component (2) which includes an aqueous acidic hydrogen peroxide solution. The formulation obtained by mixing the two components can be applied to environmental surfaces by spray, fog, mop, sponge, dip and machine treatment after combining and mixing. Use of the treatment, thus far, has demonstrated that the formulation can typically kill 99.99999% of all molds, bacteria, viruses and their spores, as well as all insect eggs and larvae within seconds. A treated environment can typically be reoccupied within about 30 minutes to about 4 hours after the formulation's application.

One aspect of the present disclosure involves a disinfectant composition including two components that are mixed before application. The first component includes an aqueous solution containing 0.01 to 5 wt. % of N, N-bis(3-aminopropyl)dodecylamine, 0.01 to 8 wt. % of at least one quaternary ammonium compound, 0.1 to 8 wt. % of a non-ionic surfactant, 1 to 10 wt. % an alkaline base, with the balance water. The pH of the first component is maintained within the range of about 8 to about 10 by inclusion of the alkaline base. The second component includes an aqueous acidic solution containing 3 to 25 wt. % hydrogen peroxide, and the balance water. The two components are maintained separate and combined just prior to application.

In a further aspect of the present disclosure, the first component can also further include 0.1 to 5 wt. % of ethylenediaminetetraacetic acid; and an alkyl($C_{12}$ to $C_{18}$ alkyl)dimethyl benzyl ammonium chloride. Still further aspects of the present disclosure can involve a first component additionally including an additional quaternary ammonium compound, such as tallowalkylrimethyl ammonium chloride and/or diethylbenzyl ammonium chloride. Still further aspects of the present disclosure can involve a first component additionally including 0.1 to 10 wt. % dipropylene glycol methyl ether, and/or 0.1 to 10 wt. % propylene glycol. Yet still other aspects of the present disclosure can involve a first component further including 0.1 to 2.0 wt. % of a tertiary amine oxide, to provide a foaming action. Suitable tertiary amine oxides include, but are not limited to N,N-dimethyldodecylamine N-oxide, 2-ethanol, 2,2'-iminobis, N-[3-(branched decyloxy)propyl] derivs., N-oxides, and bis(hydroxyethyl)-cocoalkylamine oxide.

An still further aspect of the present disclosure includes a second component including an aqueous acidic solution containing 10 to 20 wt. % hydrogen peroxide, with the balance water, whereas a still further aspect of the present disclosure includes a second component including an aqueous acidic solution containing 15 wt. % hydrogen peroxide, with the balance water. The various first and second components are maintained as separate components included in a disinfectant/sanitizer kit including separate components for mixing just before application.

A still further aspect of the present disclosure includes a disinfectant/sanitizer kit containing two formulations. The first formulation includes an aqueous alkaline solution containing N, N-bis(3-aminopropyl) dodecylamine; a quaternary ammonium compound is selected from the group consisting of alkyl($C_{12}$ to $C_{18}$ alkyl)dimethyl benzyl ammonium chloride, diethylbenzyl ammonium chloride, an alkaline base, and tallowalkylrimethyl ammonium chloride. The second formulation contains an aqueous acidic hydrogen peroxide solution having a pH less than 7. The first and second formulations are maintained in separate containers in the kit, and combined just before application.

Finally, the combined action of the trialkylamine and hydrogen peroxide has demonstrated a synergistic effect, wherein the effect of the combination is greater than the additive effect of the individual components.

DESCRIPTION

For the purposes of promoting an understanding of the present disclosure, references will now be made to the embodiments illustrated and specific language will be used to describe the same. It will nevertheless be understood that no limitation of scope of what is claimed is thereby intended, such alterations and further modifications and such further applications of the principles thereof as illustrated therein being contemplated as would normally occur to one skilled in the art to which the disclosure relates.

As used in the specification and the claims, the singular forms "a," "an" and "the" include plural referents unless the context clearly dictates otherwise. Ranges may be expressed in ways including from "about" one particular value, and/or to "about" another particular value. When such a range is expressed, another implementation may include from the one particular value and/or to the other particular value. Similarly, when values are expressed as approximations, by use of the antecedent "about," it will be understood that the particular value forms another implementation. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not. Similarly, "typical" or "typically" means that the subsequently described event or circumstance often though may not occur, and that the description includes instances where said event or circumstance occurs and instances where it does not.

Disinfectants incorporating hydrogen peroxide are attractive because hydrogen peroxide displays broad spectrum antimicrobial activity and because it decomposes into innocuous products, i.e., water and oxygen. Such broad spectrum antimicrobial activity is important in situations where harmful organisms are present, but their identity is not known. Drawbacks to the use of hydrogen peroxide include the inherent instability of hydrogen peroxide solutions and the length of time required for hydrogen peroxide, alone, to disinfect a surface. For example, stabilizers must be added to hydrogen peroxide solutions if they are to be stored for any length of time. In addition, other components must be selected that do not accelerate the peroxide's decomposition. Also, it can take up to 30 minutes or more after application for solutions of hydrogen peroxide alone to disinfect a treated surface. Stabilizers can be utilized to prolong the effective lifetime of formulations containing hydrogen peroxide, but the stabilizers often are incompatible with other components and otherwise interfere with the formulation's application. Finally, solutions containing only hydrogen peroxide fail to provide any appreciable residual effectiveness following the initial application. Formulations according to the present disclosure include hydrogen peroxide and a second biocide that together provide both a synergistic and rapid broad spectrum control of microorganisms as well as residual control following the decomposition of the hydrogen peroxide. The two components are typically combined and mixed shortly before application to a surface or to the environment, as in spraying, fogging, mopping, wiping (i.e. a sponge), dipping, applying by means of machine treatment, and the like.

The formulation's first component involves an aqueous alkaline surfactant solution containing at least one quaternary ammonium compound, at least one triamine compound, and at least one nonionic surfactant. If a foaming is desired, at least one amine oxide compound or other foaming agent can be included in the first component. The first component typically exhibits a basic pH ranging up to about 10, preferably from 8 to 10. Component 2 involves an aqueous stabilized hydrogen peroxide solution. The aqueous hydrogen peroxide solution typically contains from about 3 to about 20 wt. % of hydrogen peroxide and is typically stabilized with an acid. However, other stabilizers can also be utilized. The disinfectant formulation can be prepared by mixing the two components to provide an active disinfecting solution having a pH ranging from about 8 to about 9. Upon application, the hydrogen peroxide dissipates within hours, whereas the residual quaternary ammonium and triamine residues can remain active on the surface for several weeks.

The formulations of this present disclosure are non-corrosive, non-staining and non-bleaching yet the formulations are effective in antimicrobial disinfection and chemical decontamination. The formulation lacks the negative effects (explosive hazards and bleaching properties) associated with bleaches based on hypohalites, peroxyacetic acid and aldehydes. The formulation has no irritating odor and is not corrosive to metal or plastic. The combination of components 1 and 2 produces a disinfectant that exhibits a synergistic effect with regard to disinfection wherein a greater level of disinfection is obtained for the combination than the additive effect obtained for the individual components when tested alone.

Formulation Components:

An example of a suitable triamine is N, N-bis(3-aminopropyl) dodecylamine. One source of this triamine is sold under the trade name "Lonzabac® 12.100" and is available from Lonza Ltd. Examples of suitable amine oxides are associated with 2,2'-iminobis-, N-[(3-decyloxy)propyl] N-oxides and related amine N-oxides. Examples of suitable amine oxides include lauryl(C12) dimethylamine oxide, also known as N, N-dimethyldodecylamine N-oxide, (Marcat AO-12) from Mason Chemical; propanol and (Caloxamine® LO) from Pilot chemical Co., propanol-2-ethanol, 2,2'-iminobis, N-[3-(branched decyloxy)propyl] N-oxide (Tomamine™ AO-14) from Air Products Co.; and bis(hydroxyethyl)-cocoalkylamine oxide (Aromox® C-12-W) from Akzo Nobel Co. Examples of suitable nonionic surfactants are derived from the family of ethoxlated linear alcohols. The alcohol base molecules are $C_9$ to $C_{14}$ linear alcohols which are 1 to 10 mole ethoxylates. Examples include "Neodol® 91-6", "91-8", "25-3" "Tomadol® 91-2.5", "91-6", "23-1" from Air Products Co. Examples of suitable quaternary ammonium compounds can be found in the family of alkyl ($C_{12}$ to $C_{18}$ alkyl) dimethyl, benzyl and diethyl benzyl ammonium chlorides and tallowalkyltrimethyl ammonium chloride, Arquad T-50. Some additional examples include "Marquat cs-428" and "Marquat mq 615 m" from Mason Chemical Co., & "Barquat® 50-65B" from Lonza Corp.

Suitable quantities of materials (when utilized) for composition 1 are illustrated below:

| Ingredient | % wt./wt. concentration range |
|---|---|
| First Component: | |
| EDTA (Dissolvine ® E-39) (optional) | 0.1 to 5 |
| Potassium Carbonate powder | 1 to 10 |
| N, N-bis (3-aminopropyl) dodecylamine (Lonzabac ® 12.100) | 0.01 to 5 |
| alkyl ($C_{12}$ to $C_{18}$ alkyl) dimethyl, benzyl (Marquat CS-428) | 0.01 to 8 |
| tallowalkyltrimethyl ammonim chloride (Arquad ® T-50) (optional) | 0.1 to 10 |
| ethoxylated alcohol (6EO groups) (Tomadol ® 91-6), | 0.1 to 8 |
| dipropylene glycol methyl ether (Dowanol ® DPM), (optional) | 0.1 to 10 |
| Propylene Glycol (optional) | 0.1 to 10 |
| N,N-dimethyldodecylamine N-oxide | 0.1 to 2 |

-continued

| Ingredient | % wt./wt. concentration range |
|---|---|
| (Macat AO-12) (optional) | |
| D.I. Water | Balance |
| Second Component: | |
| 35% aqueous hydrogen peroxide | 3 to 25 |
| D.I. Water | Balance |

In the formulations above, the specific products listed are provided as examples of suitable materials, but this identification is not intended to limit the disclosure to those specific trade products. For example, other bases, such as for example other alkaline carbonates or hydroxides can be substituted for sodium carbonate, and other components can similarly be substituted with similar materials having the necessary properties. Component 1 can be prepared by mixing the appropriate ingredients in any order with low agitation until the mixture is clear and substantially homogenous. A plastic vessel, such as a plastic tank" is particularly suitable. Component 2 can be prepared by diluting hydrogen peroxide with deionized water to provide a solution containing from about 3 wt. % to about 25 wt. % hydrogen peroxide and adding sufficient acid to lower the pH to a stabilizing level. Other peroxide stabilizers typically found in commercial hydrogen peroxide can also be present. Again, containers constructed from plastic are particularly suitable.

Example 1

Sample Formulations

Component 1 (a)
The following materials were combined in the amounts indicated and mixed with slow agitation until the mixture was homogeneous and clear:
  24 grams of N, N-bis(3-aminopropyl) dodecylamine (Lonzabac® 12.100),
  36 grams of 21 grams of an ethoxylated alcohol[6EO groups, average] (Tomadol®91-6),
  34.5 grams of alkyl ($C_{12}$ to $C_{18}$ alkyl) dimethyl, benzyl and diethyl benzyl ammonium chloride (Marquat CS-428)
  405.5 grams of D.I. water
The resulting mixture can be stored in a closed container until utilized.
Component 1 (b)
The following materials were combined in the amounts indicated and mixed with slow agitation until the mixture was homogeneous and clear to provide a non-foaming component:
  15 grams of EDTA (Dissolvine® E-39),
  25 grams of Potassium Carbonate powder,
  12.5 grams of N, N-bis(3-aminopropyl) dodecylamine (Lonzabac® 12.100),
  26 grams of alkyl ($C_{12}$ to $C_{18}$ alkyl) dimethyl, benzyl and diethyl benzyl ammonium chloride (Marquat CS-428),
  35.5 grams of tallowalkyltrimethyl ammonium chloride (Arquad® T-50),
  21 grams of an ethoxylated alcohol (6EO groups) (Tomadol® 91-6),
  26.5 grams of dipropylene glycol methyl ether (Dowanol® DPM),
  19 grams of Propylene Glycol, and
  320 grams of D.I. water
The resulting mixture can be stored in a closed container until utilized. If a foaming component is desired, 5-10 grams of N,N-dimethyldodecylamine N-oxide (Macat AO-12) or another amine oxide can be added.
Component 2
The following materials were combined in the amounts indicated and mixed. The component's stability can be increased by adding additional acid to drop the pH substantially below 7. Generally, 3 to 25 wt. % of hydrogen peroxide can be utilized in component 2, whereas 10 to 20 wt. % is preferred, and finally more preferred is 15 wt. % hydrogen peroxide. Although examples are provided utilizing 35% aqueous hydrogen peroxide, other concentrations of hydrogen peroxide can be utilized as would be understood by one skilled in the art. The resulting product is stored in a container made of a plastic material free of metal ions. The following provides a specific embodiment of component 2.
  214.3 grams of 35% hydrogen peroxide (75 grams of $H_2O_2$) and
  285.9 grams of D.I. water.
Examples Utilizing the Combined Formulation:

Example (1)

300 grams of Component 1(b) and 300 grams of Component 2 are combined, mixed, and a portion of the resulting formulation applied to an area of a stained and soiled carpet. After about 3 hours the carpet is dry, the stain is removed and/or diminished, and any microorganisms present are killed. The carpet's original color is unchanged.

Example (2)

400 grams of Component 1(a) and 400 grams Component 2 are combined, mixed, and utilized to fog a room utilizing standard fogging equipment. After about 1 hour the room is disinfected and available for use.

Example (3)

500 grams of Component 1(b) and 500 grams of Component 2 are combined, mixed, and utilized to disinfect a hospital gown. The gown is dipped in the formulation, and after about 5 minutes removed, and allowed to drip dry. The resulting gown is generally free of any microorganisms.
The formulations described in examples 1-3 above, can similarly be utilized to treat other surfaces utilizing a spray application (such as a spray bottle or a rug shampooer), or treatment with a sponge or adsorbent cloth.
Trademarks appearing herein include:
  Dissolvine is a registered US trademark of Akzo Nobel Chemicals B. V. CORPORATION NETHERLANDS
  (LONZABAC is a registered US trademark of Lonza Ltd. CORPORATION SWITZERLAND
  Arquad is a registered US trademark of Akzo Nobel Chemicals B. V. CORPORATION NETHERLANDS
  Tomadol is a registered US trademark of Air Products and Chemicals, Inc. CORPORATION
  Dowanol is a common law trademark of the Dow Chemical Company or an affiliated company
  Tomamine is a registered US trademark of Air Products and Chemicals, Inc. CORPORATION
  Aromox is a registered US trademark of Akzo Nobel Chemicals B. V. CORPORATION NETHERLANDS
  Caloxamine is a registered US trademark of Pilot Chemical Holdings, Inc. CORPORATION
  Neodol is a registered US trademark of SHELL TRADEMARK MANAGEMENT B.V. NETHERLANDS Barquat is a registered US trademark of LONZA INC. CORPORATION Marcat & Marquat are formerly registered US trademarks that appear currently to be utilized primarily as product designations.

While applicant's disclosure has been provided with reference to specific embodiments above, it will be understood that modifications and alterations in the embodiments disclosed may be made by those practiced in the art without departing from the spirit and scope of the invention. All such modifications and alterations are intended to be covered.

The invention claimed is:

1. A disinfectant composition comprising two components, the first component including an aqueous solution containing:
   0.01 to 5 wt. % of N, N-bis(3-aminopropyl)dodecylamine,
   0.01 to 8 wt. % of at least one quaternary ammonium compound,
   0.1 to 8 wt. % of a non-ionic surfactant,
   1 to 10 wt. % an alkaline base,
   the balance water;
   The second component including an aqueous acidic solution containing:
   3 to 25 wt. % hydrogen peroxide, and
   the balance water;
   wherein the first and second components are combined prior to application.

2. The disinfectant composition of claim 1, wherein:
   the alkaline base is an alkaline carbonate;
   the at least one quaternary ammonium compound is selected from the group consisting of alkyl($C_{12}$ to $C_{18}$ alkyl)dimethyl benzyl ammonium chloride, diethylbenzyl ammonium chloride, and tallowalkylrimethyl ammonium chloride; and
   the non-ionic surfactant is an ethoxylated alcohol.

3. The disinfectant composition of claim 2, further including 0.1 to 5 wt. % of ethylenediaminetetraacetic acid; and
   wherein the at least one quaternary ammonium compound is alkyl($C_{12}$ to $C_{18}$ alkyl)dimethyl benzyl ammonium chloride.

4. The disinfectant composition of claim 3, wherein the at least one quaternary ammonium compound further includes tallowalkylrimethyl ammonium chloride.

5. The disinfectant composition of claim 3, wherein the at least one quaternary ammonium compound further includes diethylbenzyl ammonium chloride.

6. The disinfectant composition of claim 3, further including:
   0.1 to 10 wt. % dipropylene glycol methyl ether, and
   0.1 to 10 wt. % propylene glycol.

7. The disinfectant composition of claim 1, further including 0.1 to 2.0 wt. % of a tertiary amine oxide.

8. The disinfectant composition of claim 7, wherein the tertiary amine oxide is selected from the group consisting of N,N-dimethyldodecylamine N-oxide, 2-ethanol, 2,2'-iminobis-, N-[(3-decyloxy)propyl] N-oxide, and bis(hydroxyethyl)-cocoalkylamine oxide.

9. The disinfectant composition of claim 8, wherein the tertiary amine oxide is N,N-dimethyldodecylamine N-oxide.

10. The disinfectant composition of claim 1, wherein the second component includes an aqueous acidic solution containing:
    10 to 20 wt. % hydrogen peroxide, and
    the balance water.

11. The disinfectant composition of claim 1, wherein the second component includes an aqueous acidic solution containing:
    15 wt. % hydrogen peroxide, and
    the balance water.

12. The disinfectant composition of claim 1, wherein the first composition has a pH ranging from 8 to 10.

13. The disinfectant composition of claim 1, wherein the first and second components are separately included in a kit adapted to be mixed prior to application.

14. The disinfectant composition of claim 1, wherein the first component comprises:
    24 g of N, N-bis(3-aminopropyl)dodecylamine,
    34.5 g of alkyl ($C_{12}$ to $C_{18}$ alkyl) dimethylbenzyl ammonium chloride,
    36 g of an ethoxylated alcohol[6EO groups, average] 0.1 to 8 wt. % of a non-ionic surfactant,
    25 grams of potassium carbonate, and
    380.5 g of deionized water; and
    the second component comprises:
    214.3 g of 35% aqueous acidic hydrogen peroxide, and
    285.9 g of deionized water;
    wherein the first and second components are maintained separate to be combined prior to application.

15. The disinfectant composition of claim 1, wherein the first component comprises:
    15 g of ethylenediaminetetraacetic acid,
    25 g of potassium carbonate,
    12.5 g of N, N-bis(3-aminopropyl)dodecylamine,
    26 g of alkyl ($C_{12}$ to $C_{18}$ alkyl) dimethylbenzyl ammonium chloride,
    35.5 g of tallowalkyltrimentyl ammonium chloride,
    21 g of an ethoxylated alcohol[6EO groups, average] 0.1 to 8 wt. % of a non-ionic surfactant,
    19 g of propylene glycol,
    320 g of deionized water; and
    the second component comprises:
    285.9 g of 35% aqueous acidic hydrogen peroxide, and
    320 g of deionized water;
    wherein the first and second components are maintained separate to be combined prior to application.

16. A method for disinfecting a surface comprising:
    combining and mixing the first and second compositions of claim 1 to provide an active disinfecting solution; and
    applying the active disinfecting solution to a surface.

17. A method of claim 16, wherein applying the active disinfecting solution involves applying the solution by a process selected from the group consisting of spraying, fogging, mopping, wiping, flooding, and dipping.

18. A disinfectant/sanitizer kit containing two formulations:
    the first formulation containing an aqueous alkaline solution containing N, N-bis(3-aminopropyl) dodecylamine; a quaternary ammonium compound is selected from the group consisting of alkyl($C_{12}$ to $C_{18}$ alkyl) dimethyl benzyl ammonium chloride, diethylbenzyl ammonium chloride, and tallowalkylrimethyl ammonium chloride, and
    the second formulation containing an aqueous acidic hydrogen peroxide solution having a pH less than 7;
    wherein the combination of the first formulation and the second formulation exhibits disinfectant properties.

* * * * *